United States Patent [19]

Pinchuk et al.

[11] Patent Number: 5,071,429

[45] Date of Patent: Dec. 10, 1991

[54] METHOD FOR INSERTING A BALLOON CATHETER THROUGH AN ENDOSCOPE

[75] Inventors: Leonard Pinchuk, Miami; Stefan A. Jackowski, Hollywood, both of Fla.; John A. Shimkus, Milwaukee; Terri L. Tessmann, Racine, both of Wis.

[73] Assignee: Medical Engineering Corporation, Racine, Wis.

[21] Appl. No.: 572,527

[22] Filed: Aug. 24, 1990

[51] Int. Cl.$^5$ .................................... A61M 29/02
[52] U.S. Cl. .................................... 606/192; 128/6; 604/54; 604/96
[58] Field of Search .................................... 604/96–103, 604/158, 49, 51, 54, 55; 128/4, 6; 606/192–197

[56] References Cited

U.S. PATENT DOCUMENTS

| | | | |
|---|---|---|---|
| 4,660,560 | 4/1987 | Klein | 128/344 |
| 4,762,128 | 8/1988 | Rosenbluth | 128/343 |
| 4,893,623 | 1/1990 | Rosenbluth | 606/192 |
| 4,932,958 | 6/1990 | Reddy et al. | 606/192 |
| 5,002,558 | 3/1991 | Tegin et al. | 606/192 |
| 5,007,898 | 4/1991 | Rosenbluth et al. | 604/54 |
| 5,016,614 | 5/1991 | MacAllister | 128/4 |

FOREIGN PATENT DOCUMENTS 0341988 11/1989 European Pat. Off.
WO89/11890 12/1989 PCT Int'l Appl.

OTHER PUBLICATIONS

Burkenne et al. article in Radiology 1984:152:655–657.

Primary Examiner—John D. Yasko
Assistant Examiner—Adam J. Cermak

[57] ABSTRACT

A balloon catheter with an unreinforced stem collapses compactly. A method of introducing a balloon catheter into the body passage of a patient consists of loading the balloon end of the catheter into the unattached sheath of an endoscope and passing the elongated tubular leg attached to the balloon through the lumen of a working channel of an unattached bridge of an endoscope; then joining the bridge and the sheath to form a unitary endoscope and introducing the balloon into the body passage of a patient. A kit is disclosed which includes a balloon catheter and a separate adapter which can be used to introduce inflating fluid into the balloon.

4 Claims, 2 Drawing Sheets

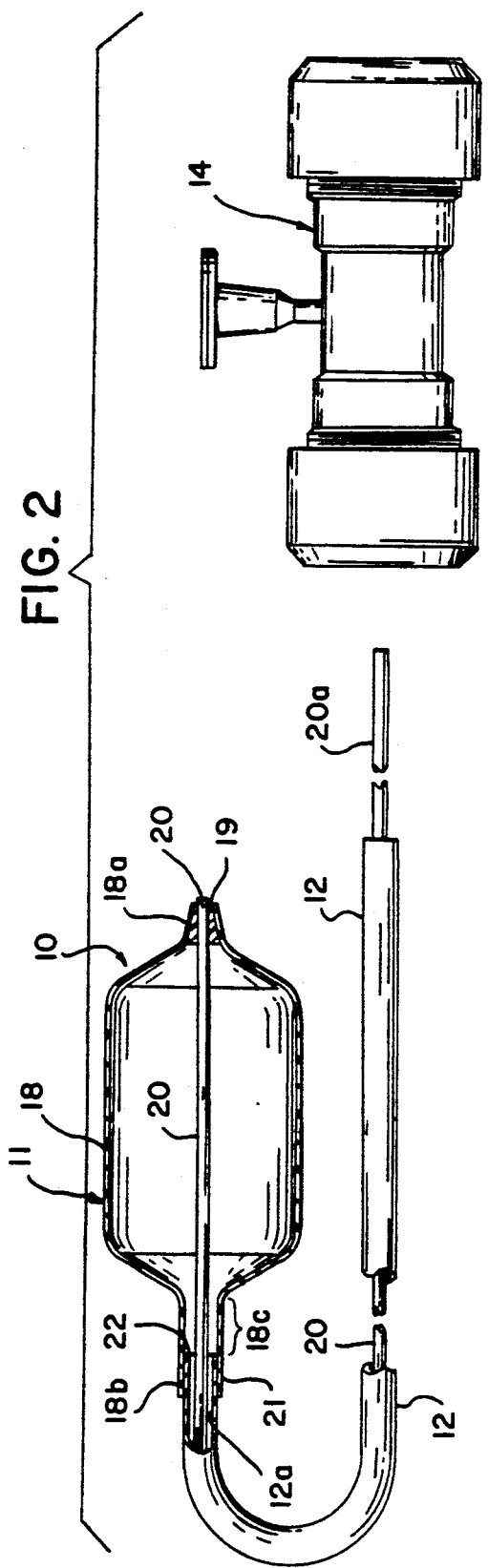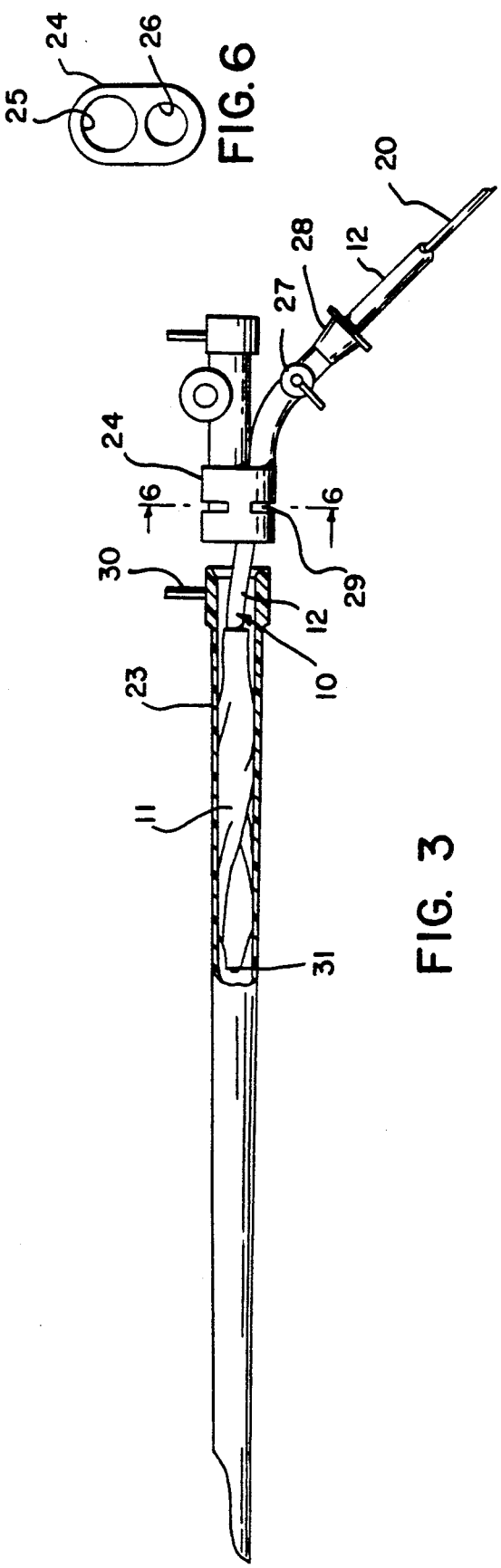

METHOD FOR INSERTING A BALLOON CATHETER THROUGH AN ENDOSCOPE

FIELD OF THE INVENTION

The invention relates generally to balloon catheters. More particularly, it relates to a balloon catheter, a kit which includes the balloon catheter and which is used for the dilatation of a body passage, such as the urethra, and a method of introducing the catheter into a body passage using an endoscope.

BACKGROUND OF THE INVENTION

In recent years, the use of balloon catheters to dilate body passages has become a popular method of medical treatment. The most common such use is angioplasty in which a balloon catheter is used to dilate a coronary artery by collapsing or compressing plaque. Another relatively new use for balloon catheters is uroplasty. This treatment relieves urinary obstruction caused by the swelling of the prostate.

In the past, transurethral resections (TUR) were commonly performed to remove sections of the prostate gland in order to relieve urinary obstruction at the bladder neck and in the prostatic urethra. Uroplasty involves inserting a balloon into the prostatic urethra (the section of the urethra that passes through the prostate gland—located distal to the neck of the urinary bladder and proximal to the urethral valve or sphincter) and inflating the balloon for 1 to 30 minutes to dilate the prostatic urethra and bladder neck.

At the present time, state of the art uroplasty involves using a 25mm balloon on a 12 to 18 French catheter. The procedure is usually performed under fluoroscopy to enable the physician to visualize placement of the balloon section of the catheter proximal to the external sphincter. Careful placement is essential in order to prevent dilating and damaging the sphincter. The balloon catheters usually contain radiopaque markers to enable the visualization of balloon location under fluoroscopy; however, urologists prefer to visualize the urinary tract through fiber optic instrumentation using a special endoscope, more specifically a cystoscope or a cysto-urethroscope.

There is a need for a uroplasty balloon catheter that can be introduced through a cystoscope, or the like, and which permits the urologist to directly visualize the prostatic urethra and the placement of the balloon without the need for fluoroscopy.

In addition, it has recently been found that better results are obtained when the prostate is dilated with a balloon that expands to approximately 35mm instead of the normal 25mm. Although balloon catheters which can inflate and dilate to 35mm can be made, it has not been possible to fabricate a catheter with a balloon of 25 mm much less 35 mm inflated diameter that will fit through the 12F working channel of the bridge of a rigid cystoscope.

Those skilled in the art of making balloon catheters recognize that a common ratio of the balloon's expanded outer diameter (OD) to the balloon's collapsed outer diameter or "leg" OD is generally in the range of 4 to 6. For example, a state of the art 25mm uroplasty balloon on a 14F catheter would have a balloon-to-leg ratio of $25 \times 3.14/14 = 5.6$, and the ranges for angioplasty balloons are generally in the range of 4 to 5. Therefore, it can be appreciated that a 35mm balloon on a 12F catheter would require a ratio of $35 \times 3.14/12 = 9.5$, which is extremely difficult to accomplish. This large balloon size introduces an additional difficulty in that even if the non-balloon portion of a 12F catheter body were to fit into the working channel of the sheath of a cystoscope, it would be extremely difficult to fold or wrap a 35mm balloon with its large surface area down sufficiently small on a 12F catheter body to fit through the 12F working channel of the bridge of the cystoscope.

It would be advantageous to have a balloon catheter in which the balloon could be folded or collapsed more compactly to further reduce its deflated profile.

Fabrication techniques, preferably blowing technologies, exist that enable inflated balloon-to-leg ratios on the order of 9 and more. However, as previously stated although balloon catheters with such favorable ratios can be made, the problem of inserting the balloon section into and through the 12F working channel of the bridge of a conventional cystoscope still remains a problem. Although with proper folding and construction of the leg of the balloon, the balloon might conceivably be forced through the working channel in the bridge, which includes a bend and a stainless steel stopcock, the effort could damage the thin-walled balloon if the fit is too snug.

Obviously, it would be advantageous to have a uroplasty catheter with a 35mm balloon and a method of introducing such a catheter into a patient using an endoscope.

SUMMARY OF THE INVENTION

It is an object of the present invention to provide a balloon catheter in which the balloon can be folded or pleated more compactly to minimize its deflated profile.

It is also an object of the present invention to provide a kit including a balloon catheter that can be introduced into the body passage of a patient with an endoscope or similar instrument.

Another object is to disclose a method of introducing the dilating balloon of a balloon catheter into a patient using an endoscope or similar instrument.

Still another object of the invention is to disclose a balloon catheter which includes radiopaque fillers which enable the user to visualize the location of the balloon using fluoroscopy.

The novel balloon catheter of the present invention comprises a balloon having an integral relatively short collapsible stem of thin walled material and an elongated tubular leg which is attached to the stem at a distance from the main portion of the balloon so that when the balloon is collapsed the stem also can be collapsed or pleated to allow excess balloon material to gather and be folded more compactly. The preferred balloon catheter also has radiopaque fillers in the leg and the tip of the catheter so that the location of the balloon in the patient can be seen with a fluoroscope.

The kit of the present invention comprises a balloon catheter having a balloon at one end with an elongated tubular leg operatively attached to the balloon and a separate adapter which can be attached to the free end or proximal end of the tubular leg and used to inflate the balloon.

The method of the present invention for introducing a dilating balloon into a patient comprises loading the uninflated, collapsed balloon end of the balloon catheter of the present invention into the channel of an unattached sheath of an endoscope, loading the free end of the elongated tubular leg of the catheter through and out a working channel of an unattached bridge of an endoscope, joining the sheath to the bridge to form a unitary endoscope containing the balloon in the sheath, and moving the collapsed balloon out of the sheath into a desired location in the body passage of the patient. In the preferred method a separate adapter is operatively attached to the free end of the elongated tubular leg prior to moving the balloon out of the endoscope into the body passage of a patient and the adapter is used to introduce inflating fluid into the balloon to dilate the body passage.

Although the kit of the present invention is intended for use in uroplasty, the kit components can be made in other sizes and shapes for angioplasty, intestinal dilatation, valvuloplasty for placement through an angioscope or other special endoscope.

BRIEF DESCRIPTION OF THE DRAWINGS

In the drawings:

FIG. 2 shows the kit comprising the balloon catheter, partly in section, and the separate adapter;

FIG. 3 shows the balloon catheter of FIG. 2 being loaded into a cystoscope;

FIG. 6 is a view taken along lines 6—6 in FIG. 3.

DESCRIPTION OF THE PREFERRED EMBODIMENT

Figure 1:
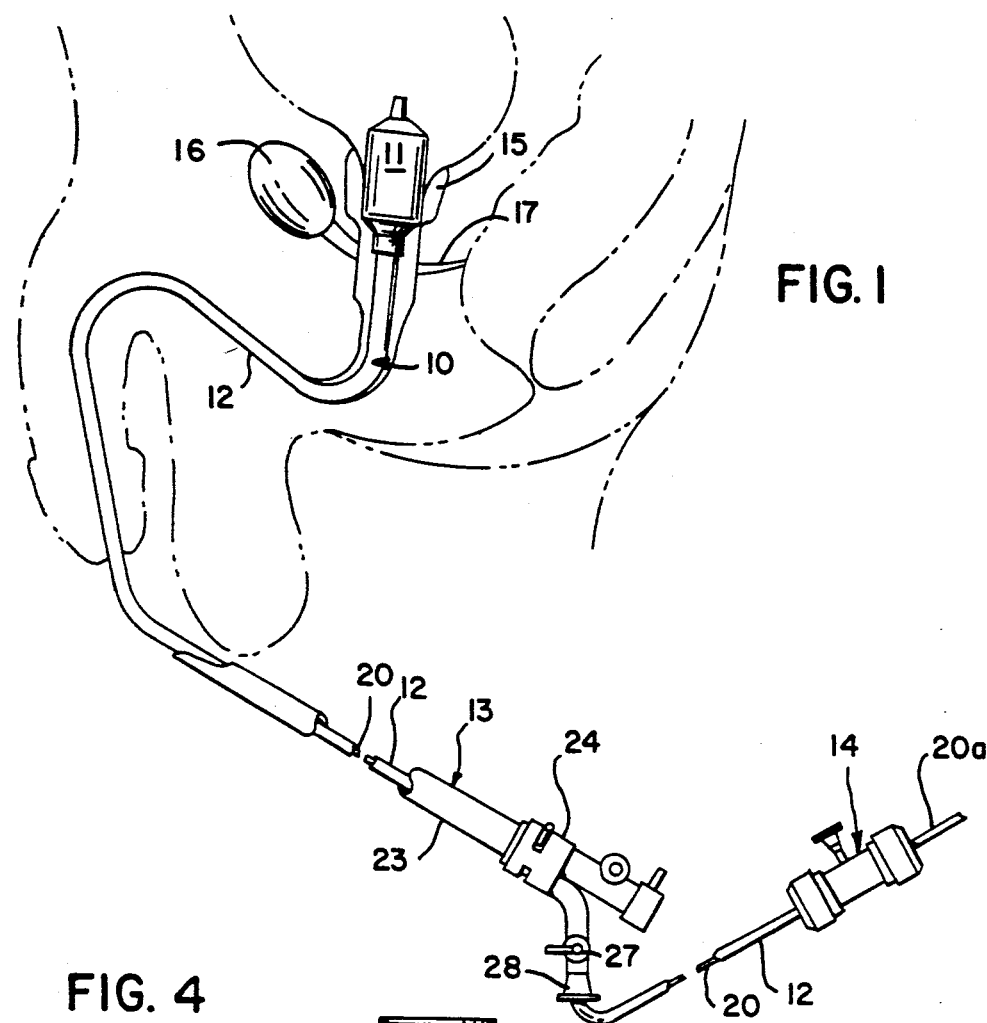
FIG. 1 shows a balloon catheter of the present invention inserted in the male urethra with the balloon inflated.

In FIG. 1 a balloon catheter 10 is shown as having an inflated balloon 11 connected to the distal end of a tubular leg 12. The tubular leg 12 passes through a cystoscope 13 and the other end of the tubular leg 12 is connected to an adapter 14.

As seen in FIG. 1, the balloon 11 is properly positioned for uroplasty within a male urethra by the prostate 15. The pubic bone 16 and the urogenital diaphragm 17 are also shown.

FIG. 2 shows a uroplasty balloon kit comprising the balloon catheter 10 with the balloon 11 and the elongated tubular leg 12 which is operatively attached to at the distal end to the balloon 11 and the separate but attachable adapter 14.

As seen best in FIG. 2, the balloon 11 comprises a collapsible, inflatable main body 18 which has a tip 18a at the distal end and a stem 18b at the proximal end. The tip 18a includes a tapered spacer 19 which is bonded to ballon 11 and tubular guide member 20. Tubular guide member 20 extends from the tip 18a through the interior of the balloon 11, the stem 18b and the lumen 12a of the tubular leg 12. The stem 18b is sealed at 21 to the distal end 22 of the tubular elongated leg 12.

Still referring to FIG. 2, it can be seen that the distal end of the tubular elongated leg 12 extends only part way into the stem 18b so that a portion 18c of the stem 18b is not reinforced by the tubular elongated leg 12. This unreinforced portion 18c which is of approximately the same thickness as the material as the balloon provides a hollow area where excess balloon material can be gathered and compacted down to minimize the insertion profile. The unreinforced portion 18c may also be pleated to further reduce the profile of the uninflated balloon.

In FIG. 2, it also can be seen that the guide member 20 extends from the tip 18a, through the main body 18 of the balloon 11, through the stem 18b and through and out the proximal free end of the tubular leg 12.

The tubular leg 12, the guide member 20, and spacer 19 can be comprised of polymeric materials provided they possess the necessary properties for proper use. The tubular leg 12 and the spacer 19 preferably contain a radiopaque filler to enable visualization of the proximal and distal extremities of the balloon 18.

Turning now to FIG. 3, a cystoscope is shown disassembled into two pieces, a sheath 23 and a bridge 24. The bridge 24 is available in many different embodiments, a commonly used bridge in cysto-urethroscopes is called the Albarran Bridge.

FIG. 6 is a cross section of the cystoscope bridge 24 along lines 6—6 in FIG. 3. The bridge 24 has a lens channel 25 and a working channel 26. The lens channel 25 is intended to accept a fiber optic bundle and the curved working channel 26 is for accepting the proximal end of the catheter. The inner diameter (ID) of the lens channel 25 is typically 12F-14F and the ID of the working channel 26 is typically 12F. The working channel 26 is fitted with a stopcock 27 and a luer fitting 28. The bridge 24 can be connected to the sheath 23 by innerconnecting a locking ring 29 on the bridge 24 and a post 30 on the sheath 23. It can be appreciated from FIG. 3 that there is more room in the larger 25F lumen 31 of the sheath 23 for passage of a balloon catheter than in the 12F working channel 26 in the bridge 24. The 12F working channel 26 with stopcock 27 is the narrowest or most restricting channel through which a balloon catheter must pass if introduced through the luer fitting 28 in a conventional manner.

According to the method of the present invention, the balloon 11 of the balloon catheter 10 is loaded into the channel 31 of the unattached sheath 23 and the proximal ends of the tubular leg 12 and guide member 20 are loaded into and through the working channel 26 of the bridge 24. The sheath 23 and bridge 24 are then locked together using the ring 29 and post 30 to form a unitary cystoscope 14.

Figure 4:
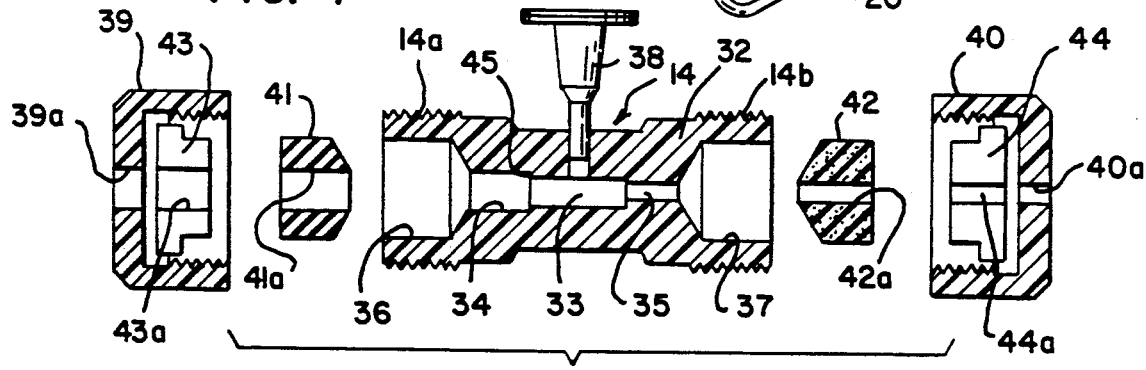
FIG. 4 is an exploded view of the adapter of FIG. 2.

FIG. 4 is an expanded schematic view of the adapter 14 which connects to an inflation device (not shown) and which is used to inflate the balloon 11. The adapter 14 has a central housing 32 with axially concentric bores 33, 34, 35, 36, and 37. Luer fitting 38 communicates with channel 33. The adapter 14 is threaded on both ends 14a and 14b to accommodate caps 39 and 40. The outer surfaces of caps 39 and 40 can be contoured or knurled to enable hand tightening of the caps onto the threaded ends 14a and 14b of housing 32. The seals 41 and 42 to be positioned within bores 36 and 37 of the housing 32 are of an elastomeric compound and the ferrules 43 and 44 which hold the seals 41 and 42 in place are preferably of a rigid material.

Figure 5:
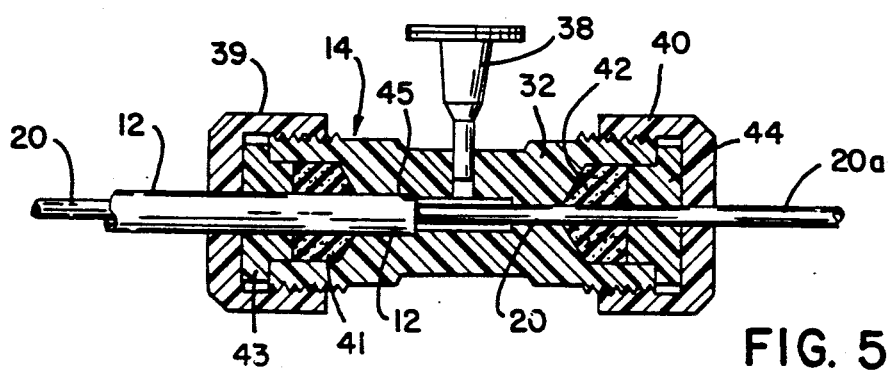
FIG. 5 is a detailed view showing the interior of the adapter of FIG. 1.

To assemble the adapter 14 on the free end of the elongated leg 12, the proximal free end of the guide member 20 is inserted through opening 39a in cap 39, through the opening 4a in ferrule 43, the opening 41a in the seal 41, bores 36, 34, 33, 35, 37, and the opening 42a in the seal 42, the opening 44a in the ferrule 44 and through opening 40a in the cap 40. A portion 20a of the guide member 20 extends out from the cap 40 where it can be grasped and used to guide the balloon 11 to a desired location in the patient. The free end of the elongated leg 12 also is inserted through the openings 39a, 43a and 41a, through bore 36 and into bore 34. It is stopped by a step 45 between bores 33 and 34. When caps 39 and 40 are tightened onto the ends 14a and 14b, respectively, the ferrules 43 and 44 compress seals 41 and 42 in bores 36 and 37, thereby forming a fluid tight junction between the outside of the elongated leg 12 and the outside of the guide member 20, respectively. It can be appreciated that seal 42, although fluid tight, may allow axial motion of guide member 20 relative to leg 12 in accordance with axial growth of balloon 11 which occurs during inflation. It can be appreciated that the adapter 14 can be made in a "quick disconnect" embodiment or the like, by those skilled in hydraulic or pneumatic engineering. The completely assembled adapter 14 is shown in FIG. 5.

In use once the balloon 11 is in proper position, a source of inflating fluid, such as a syringe of water, can be connected to the luer fitting 38, and used to inflate the balloon 11 by passing an inflating fluid through the Leur fitting 38 into the bore 33 and into a passage comprising an annular space (not shown) which exists between the outside of guide member 20 and the lumen 12a of the tubular leg 12.

The materials comprising the balloon 11, the elongated leg 12, the guide member 20 and the adapter 14 can be made of any of the materials commonly used for angioplasty catheters. For example, the balloon catheter 10 may be of nylon or polyamide, PET, polyethylene, polypropylene, polyurethane, polyvinylchloride, silicone rubber, latex rubber, etc., or combinations thereof, or biaxially oriented or radially expanded embodiments of the above. If the catheter is to be viewed by fluoroscopy the materials comprising leg 12 can be filled with radiopaque fillers, such as barium sulfate, bismuth subcarbonate, and the like. The distal tapered spacer 19 may also be made of the same material as leg 12 and can be filled with radiopaque fillers to enable visualization by fluoroscopy. The guide member 20 may be of any of the above materials, including polycarbonate and PTFE, provided it has the desired properties. The guide member 20 can be a rod-like member or preferably a tube which can provide drainage and/or receive a guidewire or stiffening rod (not shown) if one is needed to supply rigidity.

The adapter 14 can be disposable and made of any of the above materials as well as phenolics, filled resins and metals. Alternatively, the adapter 14 may be non-disposable and made of stainless steel, brass, nickel, titanium, or alloys of the above, etc. The seals 41 and 42 are relatively soft materials, such as silicone rubber, natural latex rubber, polyurethane, plasticized PVC, fluoroelastomers, or buna rubber. Attachment of the balloon to the leg and distal tip can be accomplished with suitable adhesives or by heat or ultrasonic bonding.

In the preferred embodiment the balloon 11, the tubular leg 12 and the guide member 20 are of nylon, the adapter 14 of polycarbonate and the seals 41 and 42 of silicone rubber.

Uroplasty, using the catheter of the present invention, is preferably performed as follows: The sheath 23 of the cystoscope is inserted into the urethra. The bridge 24 is then removed from the sheath 23 and the distal balloon end of the balloon catheter 10 is inserted completely into the sheath as seen in FIG. 3. If the adapter 14 is supplied attached to the proximal end of the tubular leg 12, it is then removed by loosening the caps 39, 40 and withdrawing the free proximal ends of the tubular leg 12 and the guide member 20. The proximal ends of the tubular leg 12 and the guide member 20 are threaded through the working channel 26 in the bridge 24. The bridge 24 is then connected to the sheath 23 via the locking ring 29 and post 30. Finally the adapter 14 is then positioned over the proximal ends of the tubular leg 12 and the guide member 20 as shown in FIG. 5 and the caps 39 and 40 tightened.

To insure the balloon 11 is correctly placed, a fiber optic bundle (not shown) is inserted into channel 25 of the assembled cystoscope 14 and advanced to locate the urethral sphincter. The distal end of the balloon catheter having balloon 11 is then moved out of the sheath 23, by using the portion 20a as a handle to advance the guide member 20 and leg 12 into the urethra until the balloon 11 is positioned as seen in FIG. 1. A clamp or restrictor (not shown) can be used to hold the catheter 10 stationary in respect to the cystoscope 13. The balloon 11 is then inflated by forcing fluid through leur fitting 38 into balloon 11 to the desired pressure and diameter for the required duration to dilate the body passage. When the required time for dilatation has lapsed the balloon 11 is deflated by relieving the pressure or by applying a negative pressure through luer 38 to the balloon causing the balloon to collapse. It is then pulled back into the cystoscope sheath 23 and the combination removed, thus completing the uroplasty procedure.

It will be apparent to those skilled in the art that a number of modifications and changes may be made without departing from the spirit and scope of the invention. For example, if desired, other means of inflating the balloon might be used including means not requiring an inflation tube. Also, the balloon could be made of a material that will expand to only a limited extent to prevent inadvertent overexpansion. Therefore, it is intended that the invention only be limited by the claims.

We claim:

1. A method of introducing a collapsed balloon of a balloon catheter into a body passage of a patient through an endoscope, said method comprising:
    (a) loading into the channel of the unattached sheath of an endoscope the distal end of a catheter having a collapsed but inflatable balloon at the distal end and an elongated leg at the proximal end;
    (b) loading the elongated leg into and through a working channel in an unattached bridge of an endoscope;
    (c) joining the sheath of the endoscope to the bridge to form a unitary endoscope containing the collapsed balloon in the sheath; and
    (d) moving the collapsed balloon out of the sheath into a desired location in a body passage of a patient.

2. A method of claim 1 in which the balloon portion is inflated to dilate the body passage.

3. A method of claim 2 in which the body passage is the urethra and the balloon is inflated with inflating fluid to stretch and expand the effective size of the urethra.

4. A method of claim 2 in which the balloon portion is inflated by introducing inflating fluid into the balloon through a passage in the elongated leg.

* * * * *